United States Patent
Rochette et al.

(10) Patent No.: US 10,441,514 B2
(45) Date of Patent: Oct. 15, 2019

(54) EMULSIFIER-FREE BIO MINERAL STRUCTURED EMULSION

(71) Applicant: Arclay Natural Technologies Inc., Châteauguay, QC (CA)

(72) Inventors: Sophie Rochette, Saratoga Springs, NY (US); Stephan Doyon, Saratoga Springs, NY (US); Maria Elkurdi, Côte St-Luc (CA)

(73) Assignee: Arclay Natural Technologies Inc., Châteauguay, QC (CA)

( * ) Notice: Subject to any disclaimer, the term of this patent is extended or adjusted under 35 U.S.C. 154(b) by 0 days.

(21) Appl. No.: 15/293,733

(22) Filed: Oct. 14, 2016

(65) Prior Publication Data
US 2017/0105908 A1     Apr. 20, 2017

Related U.S. Application Data

(60) Provisional application No. 62/241,317, filed on Oct. 14, 2015.

(51) Int. Cl.

| | |
|---|---|
| *A61K 8/06* | (2006.01) |
| *A61K 8/20* | (2006.01) |
| *A61K 8/25* | (2006.01) |
| *A61K 8/34* | (2006.01) |
| *A61K 8/64* | (2006.01) |
| *A61K 8/67* | (2006.01) |
| *A61K 8/73* | (2006.01) |
| *A61K 8/92* | (2006.01) |
| *A61K 8/97* | (2017.01) |
| *A61Q 19/00* | (2006.01) |
| *A61Q 5/12* | (2006.01) |
| *A61K 8/04* | (2006.01) |
| *A61K 8/36* | (2006.01) |
| *A61K 8/65* | (2006.01) |
| *A61K 8/24* | (2006.01) |
| *A61K 8/26* | (2006.01) |
| *A61K 8/365* | (2006.01) |

(52) U.S. Cl.
CPC ............. *A61K 8/062* (2013.01); *A61K 8/042* (2013.01); *A61K 8/20* (2013.01); *A61K 8/24* (2013.01); *A61K 8/25* (2013.01); *A61K 8/26* (2013.01); *A61K 8/345* (2013.01); *A61K 8/365* (2013.01); *A61K 8/65* (2013.01); *A61K 8/676* (2013.01); *A61K 8/678* (2013.01); *A61K 8/731* (2013.01); *A61K 8/732* (2013.01); *A61K 8/735* (2013.01); *A61K 8/92* (2013.01); *A61K 8/97* (2013.01); *A61Q 19/00* (2013.01); *A61K 2800/10* (2013.01); *A61K 2800/33* (2013.01); *A61Q 5/12* (2013.01)

(58) Field of Classification Search
CPC . A61K 8/062; A61K 8/97; A61K 8/92; A61K 8/735; A61K 8/676; A61K 8/65; A61K 8/345; A61K 8/25; A61K 8/20; A61K 8/678; A61K 8/24; A61K 8/26; A61K 8/365; A61K 8/731; A61K 8/732; A61K 8/042; A61K 2800/10; A61K 2800/33; A61Q 19/00; A61Q 5/12
See application file for complete search history.

(56) References Cited

U.S. PATENT DOCUMENTS

| | | |
|---|---|---|
| 2,118,566 A | 5/1938 | Miles |
| 6,841,226 B2 | 1/2005 | Dontula et al. |
| 7,658,936 B2 | 2/2010 | Von Der Fecht et al. |
| 9,387,446 B2 | 7/2016 | Bormashenko |
| 2004/0223931 A1 | 11/2004 | Mondet et al. |
| 2008/0279804 A1* | 11/2008 | Parker ............... A61K 8/25 424/70.11 |
| 2010/0129307 A1* | 5/2010 | Singer ............... A61K 8/25 424/70.13 |

FOREIGN PATENT DOCUMENTS

| | | |
|---|---|---|
| FR | 2 952 814 A1 | 5/2011 |
| FR | 2 955 771 A1 | 8/2011 |
| FR | 2 976 503 A1 | 12/2012 |
| WO | 2013/052013 A1 | 4/2013 |

OTHER PUBLICATIONS

International Search Report of PCT/US16/57059, dated Jan. 26, 2017.
Written Opinion of the International Searching Authority of PCT/US16/57059, dated Jan. 26, 2017.

\* cited by examiner

*Primary Examiner* — Blessing M Fubara
(74) *Attorney, Agent, or Firm* — Collard & Roe, P.C.

(57) ABSTRACT

A process for creating cold emulsions for cosmetic use involves creating a gel component by exfoliating silicate compounds with catalysts and organic materials under pressure and mixing the resulting components with water, mixing an oil phase with additional powdered components as desired, and mixing the gel component with the oil phase in a high shear mixer until a Pickering emulsion is created. The resulting emulsion is simple to manufacture, stable for long periods of time, and has a desirable texture for cosmetic use.

13 Claims, No Drawings

EMULSIFIER-FREE BIO MINERAL STRUCTURED EMULSION

CROSS-REFERENCE TO RELATED APPLICATIONS

This application claims priority under 35 USC 119(e) of U.S. Provisional Application Ser. No. 62/241,317, filed on Oct. 14, 2015, the disclosure of which is herein incorporated by reference.

BACKGROUND OF THE INVENTION

1. Field of the Invention

This invention relates to a formulation for creating an emulsion for cosmetic and other purposes that is made without the use of chemical emulsifiers and without the use of heating to create the emulsion. In particular, this invention relates to an emulsion of bio-minerals that is created using unique process steps that allows the combination of ingredients to be emulsified in a cold, chemical-free environment to create a product that is more stable, and requires less energy and time to prepare.

2. The Prior Art

Prior to this invention, chemical emulsions were the primary way of developing an emulsion. Chemical emulsions require heating that may affect the efficacy of active ingredients and require energy to heat the formulation. They require the use of chemical emulsifiers that may be damaging for the skin, especially the lipidic film amongst other currently known and researched skin afflictions. Chemical emulsions may also cause irritation to sensitive skin or after repeated use. Demand for natural and non-natural emulsifier-free emulsions is growing. The aging population and a growing segment of the overall population are seeking natural and non-natural emulsifier-free formulations for skin care applications.

French Patent Nos. FR2976503 and FR2952814 relate to complexes of organically modified phyllosilicates for generating cold opaque emulsions of oil in water type, for cosmetic use. The ingredients are used to create Pickering emulsions, without the use of heat. A Pickering emulsion is an emulsion that is stabilized by solid particles (for example colloidal silica) which adsorb onto the interface between the two phases. In an oil in water emulsion, a Pickering emulsion has solid components that surround each oil droplet and prevent separation of the two phases. Further examples of Pickering emulsions are described in U.S. Pat. No. 9,387,446.

While the solution in the French patents is an improvement, the resulting emulsions can be difficult to process, undesirably unstable, and can have an undesirable texture.

SUMMARY OF THE INVENTION

It is therefore an object of the invention to provide an alternative to current chemical emulsions that avoids the above-mentioned drawbacks. It is another object of the invention to allow the creation of a cold oil-in-water emulsion that is simple and efficient to create, stable for long periods of time, and has a desirable texture for cosmetic use.

This object is achieved with a bio-mineral structuring complex that allows the oil to be combined in water in a physical manner, as a Pickering emulsion, without the use of chemical emulsifiers. This invention allows for the creation of physical emulsions in a variety of textures for the natural, organic, non-natural cosmetic and other types of formulations. The emulsions according to the invention are made using a cold manufacturing process which shortens the manufacturing time and uses less energy.

The emulsions according to the invention are created by producing several phases and mixing these phases in a specific order and a specific way to create a natural cold emulsion. The process starts with the creation of a structuring agent that is mixed with water to create a water-based gel starting material. The gel can then be stored for later use. The gel is created by mixing one or more of each of the following groups of components in an extrusion mixer in a pressurized environment:

A: A phyllosilicate, inosilicate, cyclosilicate, tectosilicate, neosilicate or sorosilicate, B: A polymer, and C: An acid.

The silicates of group A can include but are not limited to sodium magnesium silicate, yofortierite, Canadian colloidal clay, calcium silicate, sodium magnesium silicate, lithium sodium magnesium silicate; Montmorillonite, Smectite, Bentonite, Illite and/or Kaolin, Pelagite, Vermiculite, ziolite. These silicates are particularly useful in forming an oil in water Pickering emulsion, because once exfoliated in the extruder, their particle sizes and packing parameters are optimal for coating an oil droplet in water. For example, the particle sizes of some of the elements are as follows:

Pelagite: 10 nm-90 nm
Vermiculite: 15 nm-1000 nm
Zeolite: 5 nm-1115 nm
Montmorillonite: 1 nm-1000 nm
Neosilicates: 5 nm-800 nm
Sorosilicates: 10 nm-900 nm.

The polymers of group B can include but are not limited to fatty acids, fatty alcohols, xanthan gum, guar gum, tapioca starch, corn starch potato starch, methyl cellulose, hydroxypropyl cellulose, carboxy cellulose, chitin, pectins and arabinoxylans.

The acids of group C can include but are not limited to citric acid, lactic acid, glycolic acid, hydrochloric acid, or phosphoric acid.

During the extrusion process, the silicates of group A become exfoliated by the acid C plus the pressure in the extruder, which opens the layers and allows the polymers B to insert between the silicate layers and swell the layers. The result is a powdered composition (LTX) that can then be used to create the modified aqueous gel phase of the emulsion preparation.

The extrusion mixer is preferably a twin-screw extrusion mixer such as Entek E27 double rotation mixer, using at least two rotative continuous screws, where the material is carried through two interrelated screws turning in the same direction. The flow rate through the mixer is 5-40 lb/h and the motor achieves an RPM up to 1200. The compounds are injected directly into the extrusion chamber, which generate intense pressure (725 psi, 50 bar) in order to combat the pressure present in the various zones of the extruder. This pressure plus the acid compounds cause the delamination of the clay compounds A during extrusion.

The gel is then created by mixing this extruded powdered component with water and a mineral salt such as magnesium sulfate or magnesium chloride or other salts for stabilization in a high shear mixer until a gel consistency is formed. The gel can be stored until the creation of an emulsion is desired. Preservatives such as benzyl alcohol or silver citrate can be added as well.

An emulsion for cosmetic or other use can then be created by mixing any desired further ingredients such a pigments, fragrance, etc. with water or an oil phase, and then mixing the oil phase with the gel with or without additional water in a high shear mixer to create the emulsion. The resulting emulsion is a Pickering emulsion, where the silicate elements from the gel surround each oil droplet and keep the emulsion stable without the need for stabilizers. The particular silicate elements of the present invention are ideally suited for creating these Pickering emulsions, due to their particle size and packing parameters. By exfoliating the silicates, their surface charge is modified which makes them ideal for this purpose. The gel can also be used in non-emulsified products as well.

The resulting emulsion does not require chemical emulsifiers and remains stable for long periods of time. By using the gel, the process ensures pre-dispersion of the clay material in a gel format to improve upon stability, freeze thaw performance and challenge test performance, and offers a large texture palette. Emulsions created without first creating the gel phase component show greater instability.

Additional materials can be added at the end of the process to adjust for sensorial, aesthetic or texture optimization.

The invention uses a multiple phase approach to formulating and producing a product formulation. The invention will allow the use of bio-mineral structuring complexes using a combination of silicates, such as montmorillonite, vermiculites, smectites or sodium magnesium silicate, combined with fat-based materials including vegetable oils, butters, waxes (animal or plant based) silicones, lipophilic mixtures, esters, hydrocarbons (mineral or synthetic), fatty alcohol benzoates, gums like xantham and other gums, hyaluronic acid, sodium hyaluronate, chitin or chitosan, maltodextrin, algin and other fat based components that may be discovered in the future, either plant, animal or chemically processed. The additional powdered materials can be selected from those described in FR 2952814 and FR2976503, the disclosures of which are herein incorporated by reference, or in any suitable manner.

The oil phase is made of oil miscible ingredients, including but not limited to oils, butters, silicones, and others. The resulting emulsions can be used for a wide variety of purposes. For example, in the field of skin care, the application can be for sunscreen, moisturizer, sebum control, ageless products, soothing, wound healing and regenerating products, anti-inflammatory, film forming, anti-stretchmark, reduce puffiness, even tone, reduce redness, and other skin care formulations. In the eye care field, some applications can include mascara, eye shadow, eye cream and other eye concept formulations. For lip care, the applications can include lip gloss, lip balm, lipstick and other lip concept formulations. Color cosmetics can include loose powders, pressed powders, powder to cream, liquid foundations and other color cosmetic formulations.

These mixtures allow the creation of natural or conventional, i.e., non-natural emulsions. The gel phase allows for the creation of pre-mixes and pre-dispersed phases which enables an easier processing in a manufacturing facility using less high shear equipment. These pre-mixes will allow small batch processing or mini emulsions offering "à la carte" formulations for consumers. The invention also provides for the creation of micro capsules for the active ingredients. This allows for the pre-encapsulation of active ingredients that are sensitive in the oil or water phase with other actives in the same phase. This pre-encapsulation allows the active ingredients to co-exist inside the same phase and then be mixed according to the phase process described herein.

Examples of the formulations can be as follows:
a. Sunscreen
b. Moisturizer
c. Soothing product
d. Mascara
e. Liquid foundation—even tone/film forming
f. Anti-age eye cream The invention allows for the creation of emulsions in other market segments like household and institutional, industrial and other market segments where the use of emulsifying technology is the norm.

The logic is based on the study of each ingredient, their incorporation levels, their sensitivity to pH levels and preservative systems.

DETAILED DESCRIPTION OF THE PREFERRED EMBODIMENTS

The invention will be described in detail with respect to several examples.

EXAMPLE 1

Eye Cream

TABLE 1

| | wt % | Ingredient |
|---|---|---|
| 1 | 21.88 | Water |
| 2 | 5.00 | Dicaprylyl Carbonate |
| 3 | 5.00 | 1,3 Propanediol |
| 4 | 3.00 | Hydrolized collagen |
| 5 | 2.00 | *Balanites roxburghii* seed oil |
| 6 | 60.00 | 4% Gel of Sodium magnesium silicate & Xanthan gum & citric acid (Structura LTX) |
| 7 | 0.50 | *Butyrospermum Parkii* (Shea Butter) |
| 8 | 0.10 | Magnesium Chloride |
| 9 | 0.10 | Xanthan Gum |
| 10 | 1.20 | Phenylpropanol (and) Propanediol (and) Caprylyl Glycol (and) Tocopherol (antimicrobial stabilizer marketed as Sensiva PA 40) |
| 11 | 0.01 | p Anisic Acid |
| 12 | 0.05 | Sodium Hyaluronate |
| 13 | 0.50 | *Porphyra umbilicalis.* (Algae extract) |
| 14 | 0.10 | *Daucus Carota* Sativa (Carrot) Seed Oil. |
| 15 | 0.05 | d,l alpha Tocopherol |
| 16 | 0.50 | Yeast extract |
| 17 | 0.01 | *Aloe Barbadensis* Leaf Extract | pH = 5.00-6.00

The LTX Gel (#6), was prepared in an extruder as described above to exfoliate the sodium magnesium silicate. The resulting powder is mixed with the water (less 11%) until homogenized, which is about 3-5 minutes. The resulting gel is then kept aside to hydrate for approximately 4 hours (for 100+Kgs).

Then, the 1,3, propanediol and Phenylpropanol/Propanediol/Caprylyl Glycol/Tocopherol (antimicrobial stabilizer) are mixed together and added to the prepared gel above.

Next, the xanthan gum, p anisic acid, sodium hyaluronate are weighed and mixed together.

Next, the hydrolyzed collagen, magnesium chloride, p anisic acid, algae extract, and yeast extract and aloe extract are dissolved in the remaining water and added in.

Next, the xanthan gum, p anisic acid, sodium hyaluronate are added to the gel and the mixture is mixed until homogenized.

The oil phase is then created by mixing together the dicaprylyl carbonate, date oil, Shea butter, carrot oil, Balanites *roxburghii* seed oil, and d,l alpha Tocopherol and this mixture is added to the gel.

The oil phase and gel are then mixed in a high shear mixer for at least 5 minutes to create the final emulsified product. The pH is adjusted with a buffer to between 5-6. As an alternative to pre-preparation of the gel, all of the ingredients can be added at once in a single mixing process.

EXAMPLE 2

Hyaluronic Eye Serum

This is an eye serum using the gel component of the invention in a serum base, rather than an in an emulsion

TABLE 2

| | wt % | Ingredient |
|---|---|---|
| 1 | 31.95 | Water |
| 2 | 7.00 | 1,3 Propanediol |
| 3 | 5.00 | Montmorillite, Illite, Kaolin (BMC) |
| 4 | 3.00 | Glycerin |
| 5 | 50.00 | LTX: Sodium magnesium silicate, xanthan gum & citric acid 4% in aqueous gel |
| 6 | 1.00 | Phenylpropanol, Propanediol, Caprylyl Glycol, Tocopherol (Sensiva Pa40) |
| 7 | 0.40 | Sodium Citrate |
| 8 | 0.10 | Sodium Hyaluronate |
| 9 | 0.05 | p anisic acid |
| 10 | 0.10 | Xanthan Gum |
| 11 | 0.10 | Magnesium Chloride |
| 12 | 0.10 | *Camellia Sinensis* Leaf Extract (green tea) |
| 13 | 1.00 | *Chamomilla recutita* (*matricaria*) Extract (chamomile) |
| 14 | 0.2 | Citric Acid |
| | 100.00 | |

The LTX component is prepared using the extrusion process described earlier to exfoliate the sodium magnesium silicate, and is mixed with water (less 1 L for future use) in the high shear mixer until homogenized, approximately 3-5 minutes. The resulting gel is then set aside for approximately 4 hours (based on 100+Kgs) until a hydrated soft gel is obtained with 4% solids content.

The sodium citrate, sodium hyaluronate, p anisic acid and xanthan gum are weighed and set aside. The magnesium chloride is dissolved in water to a concentration of 1% and set aside.

The propanediol, sodium hyaluronate, xanthan gum and Sensiva PA40 are pre-mixed. The Montmorillonite, Illite, Kaolin, Glycerin, magnesium chloride solution, green tea and chamomile are added to the gel, along with the pre-mixed propoanediol, sodium hyaluronate, xanthan gum and Sensiva PA40. Then the sodium citrate and p anisic acid powders are added. Citric acid is added to correct pH and remaining water is added. The mixture is mixed in a high shear mixer until a smooth gel is obtained. As an alternative to pre-preparation of the gel, all of the ingredients can be added at once in a single mixing process.

The resulting formulation has a smooth texture, is non-irritating and is stable for long periods of time.

EXAMPLE 3

Vitamin C Pickering Emulsion

TABLE 3

| | wt % | Ingredient |
|---|---|---|
| 1 | 77.74 | Water |
| 2 | 5.00 | Dicaprylyl Carbonate |
| 3 | 3.00 | 1,3 Propanediol |

TABLE 3-continued

| | wt % | Ingredient |
|---|---|---|
| 4 | 0.50 | Sodium citrate |
| 5 | 3.00 | Glycerin |
| 6 | 2.00 | LTX: Sodium magnesium silicate, Xanthan gum & citric acid |
| 7 | 0.50 | Sodium Ascorbyl Phosphate |
| 8 | 0.20 | *Butyrospermum Parkii* (Shea Butter). |
| 9 | 0.05 | Alpha Tocopherol (vitamin E) |
| 10 | 0.50 | Xanthan gum |
| 11 | 0.50 | *Fucus Vesiculosus* (Kelp) Extract |
| 12 | 1.20 | Phenylpropanol (and) Propanediol (and) Caprylyl Glycol (and) Tocopherol (Sensiva PA 40) |
| 13 | 0.01 | p Anisic Acid |
| 14 | 0.10 | Magnesium Chloride |
| 15 | 5.00 | Montmorillonite, Illite, Kaolin (BMC) |
| 16 | 0.50 | *Camellia Sinensis* Leaf Extract.(green tea) |
| 17 | 0.2 | Citric Acid |
| | 100.00 | | pH = 5.0-6.0

To prepare the emulsion, the following steps are performed:

The LTX gel (#6) is created by homogenizing the powders in water under pressure in an extruder till dispersed, about 3-5 minutes and set aside to hydrate for approximately 4 hours (100+Kgs) or until a soft gel is obtained. The resulting gel is approximately 4% solids content.

The propanediol, xanthan gum, sensiva PA40 and p anisic acid are pre-mixed (pre-mix A) and kept aside. Then, the Magnesium chloride is dissolved in water to create a 1% solution. The sodium citrate is also dissolved in water to create a 1% solution. The sodium ascorbyl phosphate is also dissolved in water to a 1% solution.

The oil phase is created by mixing together the dicapryl carbonate, Shea butter and alpha tocopherol (vitamin E).

The pre-mix A, magnesium chloride, sodium citrate and sodium ascorbyl phosphate are added to the gel with continuous stirring. Then the glycerin, kelp extract, BMC and green tea extract are added with stirring. Finally, the oil phase is added and the pH is adjusted. The mixture is homogenized in a high shear mixer until a uniform cream is obtained.

EXAMPLE 4

Moisturizing Conditioner

TABLE 4

| | wt % | Ingredient |
|---|---|---|
| 1 | 15.54 | Water |
| 2 | 50.00 | LTX gel Sodium magnesium silicate & Xanthan gum & citric acid (4% in water) |
| 3 | 0.40 | Sodium citrate |
| 4 | 3.00 | Glycerin |
| 5 | 2.00 | Montmorillonite & Chitin & citric acid (Structura CHI) |
| 6 | 5.00 | *Butyrospermum Parkii* (shea butter) |
| 7 | 0.05 | Alpha Tocopherol |
| 8 | 2.00 | Xanthan gum |
| 9 | 0.50 | *Fucus Vesiculosus* (Kelp) Extract |
| 10 | 10.00 | *Cocos Nucifera* (Coconut) Oil |
| 11 | 5.00 | *Persea Gratissima* (Avocado) Oil |
| 12 | 1.00 | Phenylpropanol (and) Propanediol (and) Caprylyl Glycol (and) Tocopherol (Sensiva PA40) |
| 13 | 5.00 | Montmorillonite, Illite, Kaolin (BMC) |
| 14 | 0.50 | *Camellia Sinensis* Leaf Extract. (green tea) |
| 15 | 0.01 | Sodium Hydroxide |

The gel is prepared as described above. The oil phase consisting of Structura CHI, Shea butter, alpha tocopherol, coconut oil and avocado oil are premixed and set aside. The glycerin and xanthan gum are also premixed and set aside. Then, the kelp extract, Sensiva PA40, BMC and green tea extract are added to the gel and stirred. The sodium citrate is then added and stirred. The oil phase is added to the gel, as is the glycerin and xanthan gum and the mixture is homogenized. The pH is adjusted to 4.5-5.5 and the remaining water is added. The mixture is homogenized in a high shear mixture until a uniform gel cream is obtained.

The emulsions created with the structuring agent in the form of a gel pre-cursor are very stable, simple to prepare and have a pleasing texture.

Accordingly, while only a few embodiments of the present invention have been shown and described, it is obvious that many changes and modifications may be made thereunto without departing from the spirit and scope of the invention.

What is claimed is:

1. A gel composition comprising a structuring agent mixed with water, the structuring agent comprising:
    at least one silicate selected from the group consisting of phyllosilicate, inosilicate, cyclosilicate, tectosilicate, neosilicate and sorosilicate,
    a polymer selected from the group consisting of xanthan gum, guar gum, tapioca starch, corn starch, potato starch, methyl cellulose, hydroxypropyl cellulose, carboxy cellulose, chitin, pectin and arabinoxylans, and
    an acid,
    wherein the structuring agent comprises layers of the silicate with the polymer disposed there between, and wherein structuring agent is created by extruding the silicate, polymer and acid together in a pressurized environment such that the silicate is exfoliated by the acid so that the silicate has a modified surface charge, and is intercalated by the polymer so that the polymer is disposed between the layers of the silicate.

2. The gel composition according to claim 1, wherein the silicate is a phyllosilicate selected from the group consisting of Pelagite, vermiculite, zeolite, montmorillonite, sodium magnesium silicate, yofortierite, calcium silicate, lithium sodium magnesium silicate, smectite, bentonite, illite, kaolin and Canadian colloidal clay.

3. The gel composition according to claim 1, wherein the acid is selected from the group consisting of citric acid, lactic acid, glycolic acid, hydrochloric acid and phosphoric acid.

4. The gel composition according to claim 1, wherein the structuring agent is present in an amount between 0.1-10% by weight.

5. The gel composition according to claim 1, further comprising a mineral salt and a preservative.

6. An emulsion comprising a mixture of the gel composition according to claim 1 with an oil component, the emulsion being created by mixing the gel composition with the oil component in a high shear mixture to create a Pickering emulsion.

7. The emulsion according to claim 6, wherein the oil component contains at least one component selected from the group consisting of vegetable oils, butters, waxes, and silicones.

8. A process for creating a gel composition that comprises structuring agent and water, comprising the following steps:
    mixing under pressure at least one component from each of the following groups:
    a silicate selected from the group consisting of phyllosilicate, inosilicate, cyclosilicate, tectosilicate, neosilicate and sorosilicate,
    a polymer selected from the group consisting of xanthan gum, guar gum, tapioca starch, corn starch, potato starch, methyl cellulose, hydroxypropyl cellulose, carboxy cellulose, chitin, pectin and arabinoxylans, and
    an acid, said step of mixing taking place in an extruder at elevated pressure such that the at least one silicate is exfoliated and is intercalated by the polymer, so that the structuring agent comprises layers of the silicate with the polymer disposed between the layers of the silicate.

9. The process according to claim 8, further comprising adding a stabilizer and preservative to the gel.

10. The process according to claim 8, wherein the structuring agent is mixed with water in a high shear mixer.

11. The process according to claim 8, further comprising forming a Pickering emulsion by mixing the gel with an oil in a high shear mixer.

12. The process according to claim 11, further comprising adding powdered components to the oil and gel prior to mixing.

13. The process according to claim 11, further comprising adjusting the pH of the emulsion by adding a buffer.

* * * * *